(12) United States Patent
Miles (10) Patent No.: US 9,848,967 B2
(45) Date of Patent: Dec. 26, 2017

(54) FLOSSING TOYS AND METHODS OF MAKING AND USING THE SAME

(76) Inventor: Will Miles, Leesburg, GA (US)

(*) Notice: Subject to any disclaimer, the term of this patent is extended or adjusted under 35 U.S.C. 154(b) by 1733 days.

(21) Appl. No.: 12/788,807

(22) Filed: May 27, 2010

(65) Prior Publication Data

US 2011/0290274 A1 Dec. 1, 2011

(51) Int. Cl.
*A61C 15/04* (2006.01)
*A46B 9/04* (2006.01)

(52) U.S. Cl.
CPC ............... *A61C 15/04* (2013.01); *A46B 9/04* (2013.01); *A61C 15/046* (2013.01); *A46B 2200/108* (2013.01)

(58) Field of Classification Search
CPC ..... A61C 15/04; A61C 15/043; A61C 15/046; A46B 15/0071; A46B 15/0073
USPC .......... 132/308, 309, 321, 323–327; D28/64, D28/68; 63/15, 15.45, 15.5, 15.65, 1.11, 63/1.12; 2/21
See application file for complete search history.

(56) References Cited

U.S. PATENT DOCUMENTS

| | | | | |
|---|---|---|---|---|
| 736,650 | A * | 8/1903 | Storms, Jr. ......... | A46B 15/0071 132/309 |
| 893,345 | A * | 7/1908 | Monson ............... | A61C 15/046 132/309 |
| 1,347,098 | A * | 7/1920 | Hoisington ..................... | 30/298 |
| 1,958,505 | A * | 5/1934 | Shozaburo ......... | A46B 15/0071 132/309 |
| 3,696,821 | A * | 10/1972 | Adams, IV .................... | 132/324 |
| 3,798,698 | A * | 3/1974 | Conklin, Jr. ................. | 15/167.1 |
| 3,861,406 | A * | 1/1975 | Stitt ............................. | 132/309 |
| 3,939,853 | A * | 2/1976 | Spanondis .................... | 132/323 |
| 4,016,891 | A * | 4/1977 | Kupperman ....... | A46B 15/0071 132/309 |
| 4,050,470 | A * | 9/1977 | Miller .......................... | 132/323 |
| 4,304,246 | A * | 12/1981 | Yafai ............................ | 132/323 |
| D283,761 | S * | 5/1986 | Chen ............................ | D4/108 |
| 4,617,694 | A * | 10/1986 | Bori ............................. | 15/167.1 |
| 4,706,322 | A * | 11/1987 | Nicolas ................... | A46B 9/04 132/309 |
| 4,911,927 | A * | 3/1990 | Hill et al. ..................... | 424/443 |
| 5,033,488 | A * | 7/1991 | Curtis et al. ................. | 132/321 |
| 5,222,510 | A * | 6/1993 | Zuehlsdorf .................... | 132/323 |
| 5,287,584 | A * | 2/1994 | Skinner ........................ | 15/167.1 |
| 5,435,330 | A * | 7/1995 | Dix .............................. | 132/323 |
| 5,469,874 | A * | 11/1995 | Meyer et al. ................. | 132/323 |
| 5,477,871 | A * | 12/1995 | Sanchez, Jr. ................. | 132/323 |
| 5,503,168 | A * | 4/1996 | Wang ............................ | 132/324 |
| 5,573,022 | A * | 11/1996 | Winters ........................ | 132/325 |
| 5,732,862 | A * | 3/1998 | Bull .............................. | 224/217 |
| 5,803,322 | A * | 9/1998 | Boone et al. ................. | 223/101 |
| 5,845,652 | A * | 12/1998 | Tseng et al. .................. | 132/200 |
| 5,881,745 | A * | 3/1999 | Landis .......................... | 132/323 |
| 5,893,379 | A * | 4/1999 | Ghamaty-Azimi ........... | 132/323 |
| 6,065,480 | A * | 5/2000 | Mader .......................... | 132/323 |
| 6,085,760 | A * | 7/2000 | Chodorow .................... | 132/323 |
| 6,116,252 | A * | 9/2000 | Stelmach ...................... | 132/309 |
| 6,289,546 | B1 * | 9/2001 | Harada ......................... | 15/167.1 |
| 6,397,633 | B1 * | 6/2002 | Wu ............................... | 63/1.11 |
| 7,191,784 | B2 * | 3/2007 | Landis et al. ................. | 132/323 |
| 8,091,383 | B1 * | 1/2012 | Zahiri et al. ..................... | 63/15 |

(Continued)

*Primary Examiner* — Tatiana Nobrega
(74) *Attorney, Agent, or Firm* — Withers & Keys, LLC (57) ABSTRACT

Flossing toys or devices are disclosed. Methods of making and using flossing toys or devices are also disclosed.

19 Claims, 3 Drawing Sheets

(56) References Cited

U.S. PATENT DOCUMENTS

| | | | |
|---|---|---|---|
| 2004/0187887 A1* | 9/2004 | Beckman | A46B 5/02 |
| | | | 132/309 |
| 2005/0092346 A1* | 5/2005 | Gwen | 132/323 |
| 2005/0268936 A1* | 12/2005 | Major | A61C 15/046 |
| | | | 132/325 |
| 2006/0042650 A1* | 3/2006 | Ochs | A61C 15/00 |
| | | | 132/323 |
| 2006/0185106 A1* | 8/2006 | Barbar | 15/167.1 |
| 2007/0186453 A1* | 8/2007 | Little et al. | 40/314 |
| 2007/0240732 A1* | 10/2007 | Landis et al. | 132/323 |
| 2008/0314406 A1* | 12/2008 | Barrie | 132/329 |
| 2009/0090380 A1* | 4/2009 | Culver | A46B 15/0071 |
| | | | 132/309 |
| 2009/0188520 A1* | 7/2009 | Brown | 132/321 |
| 2010/0095978 A1* | 4/2010 | Major | 132/325 |

\* cited by examiner

FLOSSING TOYS AND METHODS OF MAKING AND USING THE SAME

FIELD OF THE INVENTION

The present invention relates generally to flossing toys or devices. The present invention further relates to methods of making and using flossing toys or devices.

BACKGROUND OF THE INVENTION

Numerous flossing products exist. However, known flossing products lack one or more desirable features. For example, known flossing products fail to provide one or more of the following features: (1) a disposable flossing device that fits onto a user's finger and maintains a substantially constant tension in a piece of floss during use (e.g., during positioning onto the user's finger, flossing, etc.); (2) a disposable flossing device that fits onto a user's finger and utilizes a fixed length of floss; (3) a disposable flossing device that fits onto a user's finger and is integrally formed as a single continuous flossing device; and (4) a disposable flossing device that has kid-appeal (i.e., a child is somewhat drawn to and wants to use the flossing device).

There is a need in the art for flossing products that provide one or more of the following features: (1) a disposable flossing device that fits onto a user's finger and maintains a substantially constant tension in a piece of floss during use (e.g., during positioning onto the user's finger, flossing, etc.); (2) a disposable flossing device that fits onto a user's finger and utilizes a fixed length of floss; (3) a disposable flossing device that fits onto a user's finger and is integrally formed as a single continuous flossing device; and (4) a disposable flossing device that has kid-appeal (i.e., a child is somewhat drawn to and wants to use the flossing device).

SUMMARY OF THE INVENTION

The present invention is directed to flossing products that address one or more of the above-noted problems in the art of flossing tools. In one exemplary embodiment of the present invention, the flossing product comprises a flossing toy comprising (i) a central base portion, (ii) two, spaced floss-supporting members extending downward from the central base portion, (iii) a fixed length of floss extending between and connected to each of the two, spaced floss-supporting members, and (iv) two finger-engaging members extending upward from the central base portion, wherein the two finger-engaging members combine with one another to form an open loop having a slot therein, the slot being positioned a distance from the central base portion and a further distance from the fixed length of floss, the open loop being sized to adjustably extend over and grasp a finger positioned therein.

In another exemplary embodiment of the present invention, the flossing product comprises a flossing toy comprising (i) a central base portion, (ii) two, spaced floss-supporting members extending downward from the central base portion, (iii) a fixed length of floss extending between and connected to each of the two, spaced floss-supporting members, and (iv) two finger-engaging members extending upward from the central base portion, wherein the two finger-engaging members combine with one another to form an open loop having a slot therein, the slot being positioned a distance from the central base portion and a further distance from the fixed length of floss, the open loop being sized to adjustably extend over and grasp a finger positioned therein, and wherein (I) (i) the central base portion, (ii) the two, spaced floss-supporting members, and (iii) the two finger-engaging members form an integrally connected flossing member, and (II) the central base portion has an outer perimeter that extends horizontally beyond at least one outer edge of at least one of the two, spaced floss-supporting members.

In yet another exemplary embodiment of the present invention, the flossing product comprises a flossing toy comprising (i) a central base portion, (ii) two, spaced floss-supporting members extending downward from the central base portion, (iii) a fixed length of floss extending between and connected to each of the two, spaced floss-supporting members, wherein opposite ends of the fixed length of floss are embedded within end portions of the two, spaced floss-supporting members, and (iv) two finger-engaging members extending upward from the central base portion, wherein the two finger-engaging members combine with one another to form an open loop having a slot therein, the slot being positioned a distance from the central base portion and a further distance from the fixed length of floss, the open loop being sized to adjustably extend over and grasp a finger positioned therein.

The present invention is also directed to methods of making flossing products. In one exemplary embodiment of the present invention, the method of making a flossing product comprises the step of forming at least one molded part comprising (i) a central base portion, (ii) two, spaced floss-supporting members extending downward from the central base portion, and (iii) two finger-engaging members extending upward from the central base portion, wherein the two finger-engaging members combine with one another to form an open loop having a slot therein, the slot being positioned a distance from the central base portion and a further distance from a fixed length of floss extending between the two, spaced floss-supporting members. The method of making a flossing product may further comprise one or more additional steps including, but not limited to, combining one or more molded parts to one another; cutting a fixed length of floss from a longer length of floss; connecting the fixed length of floss to each of the two, spaced floss-supporting members; printing and/or adhering an image onto an outer surface of the at least one molded part; and packaging the flossing product.

The present invention is further directed to methods of using flossing products. In one exemplary embodiment of the present invention, the method comprises a method of flossing, wherein the method comprises positioning a flossing toy or device over a finger, the flossing toy or device comprising (i) a central base portion, (ii) two, spaced floss-supporting members extending downward from the central base portion, (iii) a fixed length of floss extending between and connected to each of the two, spaced floss-supporting members, and (iv) two finger-engaging members extending upward from the central base portion, wherein the two finger-engaging members combine with one another to form an open loop having a slot therein, the slot being positioned a distance from the central base portion and a further distance from the fixed length of floss, the open loop being sized to adjustably extend over and grasp a finger positioned therein; and pushing down on the flossing toy or device so that the fixed length of floss passes between two adjacent teeth.

These and other features and advantages of the present invention will become apparent after a review of the following detailed description of the disclosed embodiments and the appended claims.

BRIEF DESCRIPTION OF THE FIGURES

The present invention is further described with reference to the appended figures, wherein.

DETAILED DESCRIPTION OF THE INVENTION

Figure 1:
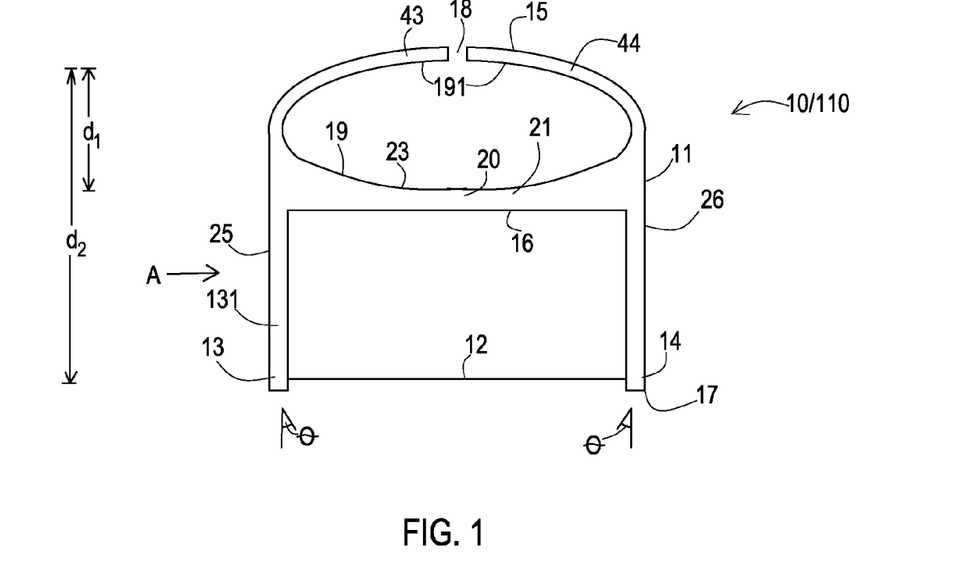
FIG. 1 depicts a side view of an exemplary flossing toy of the present invention.

The present invention is directed to flossing devices. The present invention is further directed to methods of making, as well as methods of using flossing devices. An exemplary flossing device of the present invention is shown in FIG. 1. As shown in FIG. 1, exemplary flossing device 10/100 comprises a central base portion 20, two, spaced floss-supporting members 13 and 14 extending downward from central base portion 20, a fixed length of floss 12 extending between and connected to each of spaced floss-supporting members 13 and 14, and two finger-engaging members 43 and 44 extending upward from central base portion 20. In exemplary flossing device 10/100, the two finger-engaging members 43 and 44 combine with one another to form an open loop 19 having a slot 18 therein, with slot 18 being positioned a distance ($d_1$) from central base portion 20 and a further distance ($d_2$) from fixed length of floss 12. Further, in exemplary flossing device 10, open loop 19 is sized to adjustably extend over and grasp a finger (not shown) positioned therein.

As shown in FIG. 1, the flossing devices of the present invention may comprise a number of components. A description of individual components and combinations of individual components is provided below.

I. Device Components

The flossing devices of the present invention may comprise one or more of the following components.

A. Central Base Component

Figure 2A:
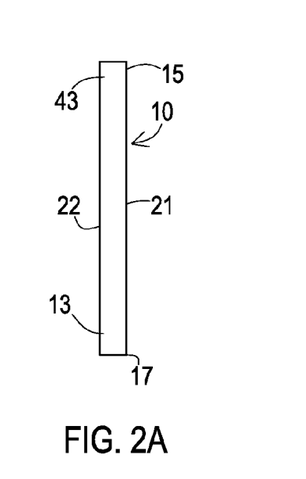
FIG. 2A depicts an end view of an exemplary profile of the exemplary flossing toy shown in FIG. 1 as viewed along direction A shown in FIG. 1.
Figure 2B:
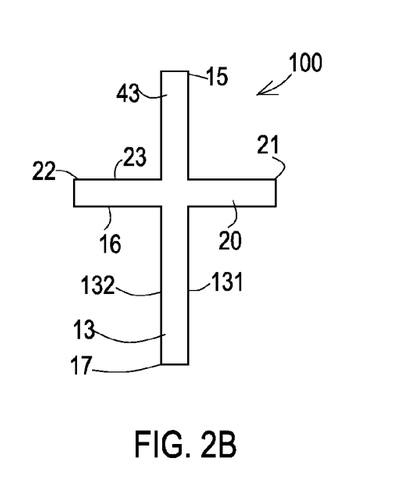
FIG. 2B depict an end view of another profile of the exemplary flossing toy shown in FIG. 1 as viewed along direction A shown in FIG. 1.

The flossing devices of the present invention comprise a central base portion such as exemplary central base portion 20 shown in FIG. 1. As shown in FIGS. 2A-2B, exemplary central base portion 20 of exemplary flossing device 10/100 may have various profiles. For example, in FIG. 2A, exemplary central base portion 20 of exemplary flossing device 10 has a width equal to or less than an overall width of exemplary flossing device 10. In this exemplary embodiment, exemplary central base portion 20 of exemplary flossing device 10 desirably has a width that is substantially equal to an overall width of exemplary flossing device 10, a width of the two, spaced floss-supporting members 13 and 14 extending downward from central base portion 20, and the two finger-engaging members 43 and 44 extending upward from central base portion 20.

In the exemplary embodiment shown in FIG. 2B, exemplary central base portion 20 of exemplary flossing device 100 has a width greater than (i) a width of the two, spaced floss-supporting members 13 and 14 extending downward from central base portion 20, and (ii) a width of the two finger-engaging members 43 and 44 extending upward from central base portion 20. In this exemplary embodiment, exemplary central base portion 20 of exemplary flossing device 100 represents an overall width of exemplary flossing device 100.

Figure 3A:
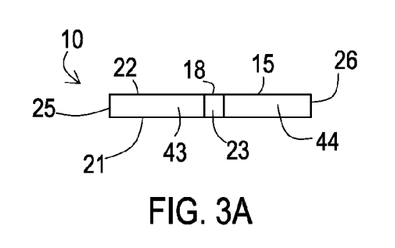
FIGS. 3A-3B depict top views respectively of the exemplary profiles shown in FIGS. 2A-2B.
Figure 3B:
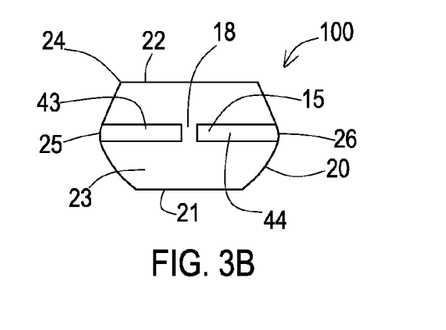
Figure 4A:
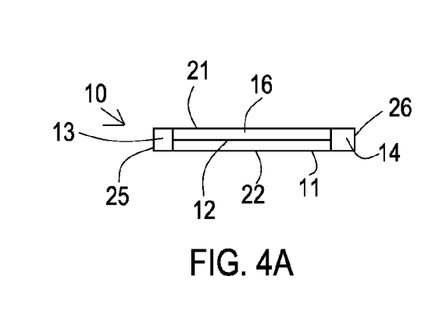
FIGS. 4A-4B depict bottom views respectively of the exemplary profiles shown in FIGS. 2A-2B.
Figure 4B:
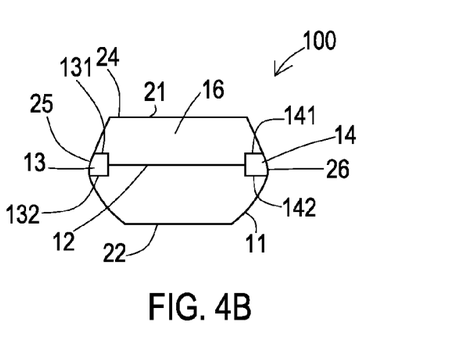

FIGS. 3A-3B provide top views respectively of the exemplary profiles of exemplary devices 10 and 100, respectively, shown in FIGS. 2A-2B. FIGS. 4A-4B provide bottom views, respectively, of the exemplary profiles of exemplary devices 10 and 100 shown in FIGS. 2A-2B.

Figure 5A:
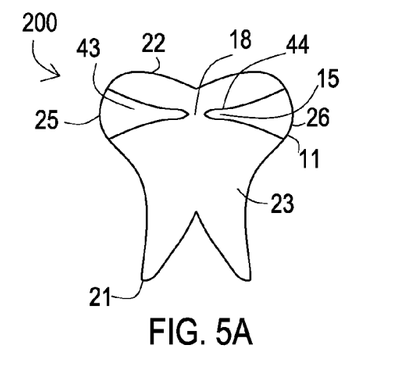
FIGS. 5A-5B depict top and bottom views respectively of an exemplary flossing toy having a tooth shape.
Figure 5B:
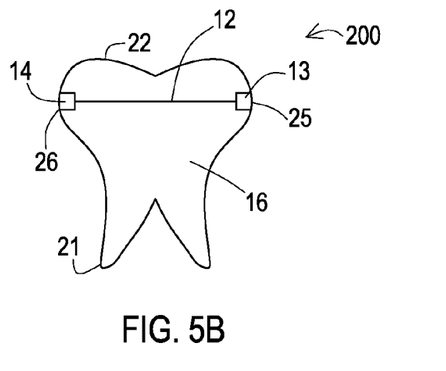
Figure 6A:
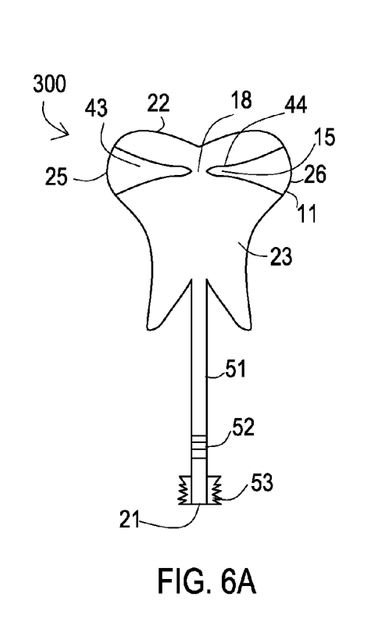
FIGS. 6A-6B depict top and bottom views respectively of another exemplary flossing toy having a tooth shape and an exemplary brush extension.
Figure 6B:
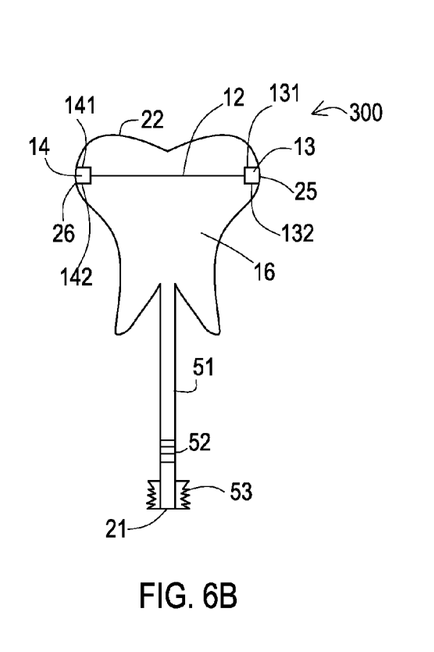

As shown in FIGS. 5A-6B, the flossing toy or device of the present invention may have a variety of overall shapes. For example, FIGS. 5A-5B provide top and bottom views respectively of an exemplary flossing toy 200 having a tooth shape. In addition, FIGS. 6A-6B provide top and bottom views respectively of another exemplary flossing toy 300 having a tooth shape and an exemplary brush extension.

As shown in the figures, some flossing toys or devices of the present invention comprise a central base portion, such as exemplary central base portion 20 of exemplary flossing device 100, wherein the central base portion has an outer perimeter 24 that extends horizontally beyond at least one outer edge of at least one of the two, spaced floss-supporting members. See, for example, how outer perimeter 24 of exemplary central base portion 20 of exemplary flossing device 100 extends horizontally beyond outer edges 131 and 132 of spaced floss-supporting member 13 as shown in FIGS. 2B and 4B.

In some exemplary embodiments, outer perimeter 24 extends horizontally beyond at least two outer edges of each of the two, spaced floss-supporting members. See again, for example, how outer perimeter 24 of exemplary central base portion 20 of exemplary flossing device 100 extends horizontally beyond (i) outer edges 131 and 132 of spaced floss-supporting member 13 and (ii) outer edges 141 and 142 of spaced floss-supporting member 14 as shown in FIG. 4B. In other exemplary embodiments, outer perimeter 24 extends horizontally beyond all outer edges of each of the two, spaced floss-supporting members. See, for example, how outer perimeter 24 of exemplary central base portion 20 of exemplary flossing device 400 extends horizontally beyond (i) outer edges 131, 132 and 133 of spaced floss-supporting member 13 and (ii) outer edges 141, 142 and 143 of spaced floss-supporting member 14 as shown in FIG. 7B.

In any of the above-described exemplary embodiments, an upper surface 23 of central base portion 20, a lower surface 16 of central base portion 20, or both upper and lower surfaces 23 and 16, respectively, of central base portion 20 may have (i) surface undulations, (ii) printed material, or (iii) both (i) and (ii) thereon (not shown). For example, surface undulations may be formed in upper surface 23 and/or lower surface 16 of central base portion 20 during a thermoforming step (e.g., molding step) while forming central base portion 20. Alternatively, surface undulations may be formed in upper surface 23 and/or lower surface 16 of central base portion 20 following a thermoforming step (e.g., molding step) used to form central base portion 20. Printed material may be incorporated into central base portion 20 during formation (e.g., during a thermoforming step) or following formation of central base portion 20 (e.g., via a printing step or an adhering step wherein printed material on an adhesive backing is adhered to upper surface 23 and/or lower surface 16 of central base portion 20).

As shown in FIGS. 6A-6B, central base portion 20 may further comprise one or more integrally connected tool members extending therefrom. In this exemplary embodiment, central base portion 20 comprises an integrally connected brush 21 with brush stem 51 and optional bendable brush stem section 52 positioned along brush stem 51 between central base portion 20 and brush 21. In other exemplary embodiments, the one or more integrally connected tool members may comprise a tool including, but not limited to, a toothpick, and a rubber/plastic wedge for gum stimulation.

Central base portion 20 may be formed from any desired material. Typically, central base portion 20 comprises a thermoformable material such as a polymeric material. Suitable polymeric materials for forming central base portion 20 include, but are not limited to, a polyolefin (e.g., polyethylene, polypropylene, copolymers of ethylene and propylene), a polyester (e.g., PET), polyvinyl chloride, a polyacrylate (e.g., polymethyl methacrylate), or any other thermoformable polymer. Although polymeric material is typically used to form central base portion 20, other suitable materials for forming central base portion 20 include, but are not limited to, a metallic material (e.g., aluminum), a cellulosic material (e.g., wood), and a ceramic material.

In some exemplary embodiments, the material used to form central base portion 20 may further comprise one or more additives including, but not limited to, (1) a fluoride-containing component (i.e., similar to fluoride-containing components typically found in toothpastes); (2) an anti-bacterial component; (3) a colorant; (4) a flavor (e.g., strawberry); (5) a scent (e.g., vanilla, strawberry, etc.); and (6) any combination of (1) to (5). For example, when central base portion 20 comprises one or more of the above-described integrally connected tool members, it may be desirable to incorporate one or more of the above-mentioned additives into the material used to form central base portion 20.

B. Floss-Supporting Members

The devices of the present invention further comprise two, spaced floss-supporting members such as exemplary floss-supporting members 13 and 14 shown in FIG. 1. Exemplary floss-supporting members 13 and 14 may have any dimensions (e.g., length, cross-sectional width, etc.) and shape (e.g., square cross-sectional shape, circular cross-sectional shape, etc.), as long as exemplary floss-supporting members 13 and 14 are structurally capable of (i) supporting a fixed length of floss (e.g., exemplary fixed length of floss 12), and (ii) withstanding an amount of force thereon during a flossing step.

Although exemplary floss-supporting members 13 and 14 may be separate pieces that are connected to exemplary central base portion 20, typically, exemplary floss-supporting members 13 and 14 are integrally connected to exemplary central base portion 20, and extend downward from exemplary central base portion 20 as shown in the figures.

Like exemplary central base portion 20, exemplary floss-supporting members 13 and 14 may be formed from any desired material. Any of the above-mentioned polymeric materials, metallic materials (e.g., aluminum), cellulosic materials (e.g., wood), and/or ceramic materials for forming central base portion 20 may be used to form exemplary floss-supporting members 13 and 14. Typically, exemplary floss-supporting members 13 and 14 each independently comprise a thermoformable material such as one of the above-mentioned polymeric materials (i.e., for forming exemplary central base portion 20) with or without one or more of the above-mentioned additives.

C. Floss

The devices of the present invention further comprise a fixed length of floss such as exemplary fixed length of floss 12 shown in FIG. 1. As used herein, the term "fixed length of floss" refers to a length of floss extending between exemplary floss-supporting members 13 and 14, wherein the length of floss extending between exemplary floss-supporting members 13 and 14 remains substantially constant throughout the life of the flossing toy or device.

In some exemplary embodiments, fixed length of floss 12 is substantially equal to or less than an overall width of the flossing toy (e.g., less than a distance between first outer edge 25 and second outer edge 26 in the exemplary flossing devices shown in FIGS. 1 and 3A-7B). As used herein, the term "substantially equal" means up to about 1.2× (or about 1.15×, or about 1.1×, or about 1.05×) the overall width of the flossing toy (e.g., the distance between first outer edge 25 and second outer edge 26 in the exemplary flossing devices shown in FIGS. 1 and 3A-7B).

Typically, fixed length of floss 12 is substantially equal to or less than a distance between outermost opposite edges of exemplary floss-supporting members 13 and 14, for example, up to about 1.2× (or about 1.15×, or about 1.1×, or about 1.05×) of the distance between outermost opposite edges 133 and 143 of exemplary floss-supporting members 13 and 14 (or less than 1.0× the distance between outermost opposite edges 133 and 143 of exemplary floss-supporting members 13 and 14).

In some exemplary embodiments, opposite ends of fixed length of floss 13 are embedded within end portions of the two, spaced floss-supporting members (i.e., end portions of exemplary floss-supporting members 13 and 14). In this embodiment, fixed length of floss 12 has a length substantially equal to or between (i) a first distance between outermost opposite edges of exemplary floss-supporting members 13 and 14, for example, the distance between outermost opposite edges 133 and 143 of exemplary floss-supporting members 13 and 14 (as shown in FIG. 7B) and (ii) a second distance between innermost opposite edges of exemplary floss-supporting members 13 and 14, for example, the distance between innermost opposite edges 134 and 144 of exemplary floss-supporting members 13 and 14 (as shown in FIG. 7B).

The floss may comprise any commercially available floss material. In some exemplary embodiments, the floss material may further comprise one or more of the above-mentioned optional additives, namely, (1) a fluoride-containing component (i.e., similar to fluoride-containing components typically found in toothpastes); (2) an anti-bacterial component; (3) a colorant; (4) a flavor (e.g., strawberry); (5) a scent (e.g., vanilla, strawberry, etc.); and (6) any combination of (1) to (5).

D. Finger-Engaging Members

The devices of the present invention further comprise finger-engaging members such as exemplary finger-engaging members 43 and 44 shown in FIG. 1. Exemplary finger-engaging members 43 and 44 may have any dimensions (e.g., length, cross-sectional width, etc.) and shape (e.g., square cross-sectional shape, circular cross-sectional shape, both, etc.), as long as exemplary finger-engaging members 43 and 44 are structurally capable of (i) extending over and around at least a portion of an outer perimeter of a user's finger, (ii) withstanding an amount of loop-opening force exerted thereon during a loop-opening step as exemplary finger-engaging members 43 and 44 are extended over and onto a user's finger, and (iii) withstanding an amount of flossing force exerted thereon during a flossing step.

Although exemplary finger-engaging members 43 and 44 may be separate pieces that are connected to exemplary central base portion 20, typically, exemplary finger-engaging members 43 and 44 are integrally connected to exemplary central base portion 20, and extend upward from exemplary central base portion 20 as shown in the figures.

Like exemplary central base portion 20 and exemplary floss-supporting members 13 and 14, exemplary finger-engaging members 43 and 44 may be formed from any desired material. Any of the above-mentioned polymeric materials, metallic materials (e.g., aluminum), cellulosic materials (e.g., wood), and/or ceramic materials for forming central base portion 20 and exemplary floss-supporting members 13 and 14 may be used to form exemplary finger-engaging members 43 and 44. Typically, exemplary finger-engaging members 43 and 44 each independently comprise a thermoformable material such as one of the above-mentioned polymeric materials (i.e., for forming exemplary central base portion 20 and exemplary floss-supporting members 13 and 14) with or without one or more of the above-mentioned additives.

As shown in the figures, each of exemplary flossing devices 10, 100, 200, 300 and 400 comprises exemplary two finger-engaging members 43 and 44, which combine with one another to form an open loop 19 having a slot 18 therein. Slot 18 may be positioned along any portion of open loop 19. Slot 18 is positioned a distance ($d_1$) from central base portion 20 and a further distance ($d_2$) from fixed length of floss 12 as shown in FIG. 1. In some exemplary embodiments, slot 18 is positioned a maximum distance (i.e., maximum distance ($d_{2max}$) from fixed length of floss 12 (such as is shown in exemplary flossing device 10/100 shown in FIG. 1).

Open loop 19 may have any desired shape as long as open loop 19 fits on to and secures the flossing device (i.e., exemplary flossing device 10/100) to a user's finger (not shown). In some exemplary embodiments, open loop 19 has an oblong shape as shown in FIG. 1.

In some exemplary embodiments, the two finger-engaging members (e.g., exemplary two finger-engaging members 43 and 44) are parallel with fixed length of floss (e.g., exemplary fixed length of floss 12). Such embodiments are shown in the figures.

II. Methods of Making Flossing Devices

The present invention is further directed to methods of making the above-described flossing devices. In one exemplary embodiment of the present invention, the method of making a flossing product comprises the step of forming at least one molded part comprising (i) a central base portion (e.g., exemplary central base portion 20), (ii) two, spaced floss-supporting members extending downward from the central base portion (e.g., exemplary floss-supporting members 13 and 14), and (iii) two finger-engaging members extending upward from the central base portion (e.g., exemplary two finger-engaging members 43 and 44), wherein the two finger-engaging members combine with one another to form an open loop having a slot therein, the slot being positioned a distance from the central base portion and a further distance from a fixed length of floss extending between the two, spaced floss-supporting members.

The method of making a flossing product may further comprise one or more additional steps including, but not limited to, combining one or more molded parts to one another; cutting a fixed length of floss from a longer length of floss; connecting the fixed length of floss to each of the two, spaced floss-supporting members; printing and/or adhering an image onto an outer surface of the at least one molded part; coating one or more molded parts or incorporating therein one or more of the following optional additive materials: (1) a fluoride-containing component (i.e., similar to fluoride-containing components typically found in toothpastes), (2) an anti-bacterial component, (3) a colorant, (4) a flavor (e.g., strawberry), (5) a scent (e.g., vanilla, strawberry, etc.), and (6) any combination of (1) to (5); and packaging the flossing product.

In some exemplary embodiments, the method of making a flossing product comprises the step of forming an integrally connected flossing member comprising (i) the central base portion (e.g., exemplary central base portion 20), (ii) the two, spaced floss-supporting members extending downward from the central base portion (e.g., exemplary floss-supporting members 13 and 14), and (iii) the two finger-engaging members extending upward from the central base portion (e.g., exemplary two finger-engaging members 43 and 44). Typically, the integrally connected flossing member is formed via a single thermoforming step, such as a single injection molding step.

In some exemplary embodiments, the method of making a flossing product comprises the step of forming a flossing member consists essentially of (i) the central base portion (e.g., exemplary central base portion 20), (ii) the two, spaced floss-supporting members extending downward from the central base portion (e.g., exemplary floss-supporting members 13 and 14), (iii) the fixed length of floss (e.g., fixed length of floss 12), and (iv) the two finger-engaging members extending upward from the central base portion (e.g., exemplary two finger-engaging members 43 and 44). The forming step may comprise (or consist essentially of or consist of) one or more thermoforming steps, and desirably comprises (or consists essentially of or consists of) a single thermoforming step wherein opposite ends of the fixed length of floss (e.g., opposite ends of fixed length of floss 12) are embedded within end portions of the two, spaced floss-supporting members (e.g., within end portions of exemplary floss-supporting members 13 and 14).

In some exemplary embodiments, the method of making a flossing product comprises (or consists essentially of or consists of) the step of forming a flossing member consisting of (i) the central base portion (e.g., exemplary central base portion 20), (ii) the two, spaced floss-supporting members extending downward from the central base portion (e.g., exemplary floss-supporting members 13 and 14), (iii) the fixed length of floss (e.g., fixed length of floss 12), (iv) the two finger-engaging members extending upward from the central base portion (e.g., exemplary two finger-engaging members 43 and 44), (v) one or more of the optional additive materials incorporated or coating onto any of components (i) to (iv), and (vi) optional printed material along a surface of the flossing toy (e.g., along any surface of any of exemplary flossing devices 10, 100, 200, 300 and 400, such as upper surface 23 and/or lower surface 16 of central base portion 20 in any of exemplary flossing devices 10, 100, 200, 300 and 400).

III. Methods of Using Flossing Devices

The present invention is even further directed to methods of using the above-described flossing devices. In one exemplary embodiment, the method comprises a method of flossing, wherein the method comprises positioning a flossing toy or device over a finger, the flossing toy or device comprising (i) a central base portion, (ii) two, spaced floss-supporting members extending downward from the central base portion, (iii) a fixed length of floss extending between and connected to each of the two, spaced floss-supporting members, and (iv) two finger-engaging members extending upward from the central base portion, wherein the two finger-engaging members combine with one another to form an open loop having a slot therein, the slot being positioned a distance from the central base portion and a further distance from the fixed length of floss, the open loop being sized to adjustably extend over and grasp a finger positioned therein; and exerting a flossing force on the flossing toy or device so that the fixed length of floss passes between two adjacent teeth.

Methods of flossing may further comprises one or more additional steps including, but not limited to, exerting a removal force on the flossing toy or device so as to remove the fixed length of floss from between two adjacent teeth; removing the flossing toy or device from a packaging material; using one or more optional tools on the flossing toy or device (e.g., using an integrally connected brush (e.g., brush 53 shown in FIG. 6A-6B); cleaning the flossing toy or device; removing debris from the fixed length of floss; and disposing of the flossing toy or device after a desired number of uses (e.g., from a single use to any number of uses).

Desirably, in some embodiments, central base portion (e.g. exemplary central base portion 20) and the two, spaced floss-supporting members (e.g., exemplary floss-supporting members 13 and 14) have a threshold degree of rigidity such that the central base portion and the two, spaced floss-supporting members do not bend during a flossing step (i.e., the flossing force exerted on the flossing toy is less than a threshold force necessary to bend the central base portion and the two, spaced floss-supporting members).

Desirably, in other embodiments, the two, spaced floss-supporting members (e.g., exemplary floss-supporting members 13 and 14) have a threshold amount of rigidity such that the two, spaced floss-supporting members (e.g., exemplary floss-supporting members 13 and 14) resiliently bend up to about 15° (i.e., angle θ is less than about 15°, see FIG. 1) during a flossing step (i.e., the flossing force exerted on the flossing toy is slightly greater than or less than a threshold force necessary to bend the two, spaced floss-supporting members).

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Preparation of a Flossing Device

An exemplary flossing toy 10 as shown in FIGS. 1, 2A, 3A and 4A was prepared as follows. A single injection molding step was utilized to form central base portion 20, two, spaced floss-supporting members 13 and 14 extending downward from central base portion 20, and two finger-engaging members 43 and 44 extending upward from central base portion 20. A fixed length of floss 12 was positioned in a stationary position within the mold prior to the injection molding step so that opposite ends of fixed length of floss 12 were embedded within end portions of two, spaced floss-supporting members 13 and 14.

The resulting floss toy had the following dimensions:

overall width (distance between outer edges 25 and 26 shown in FIG. 4A)—19 mm;

overall length (distance between outer edges 21 and 22 shown in FIG. 4A)—2 mm;

overall height (distance between upper end 15 and lower end 17 shown in FIG. 1)—22 mm;

length of fixed length of floss 12—19 mm;

length of each of the two, spaced floss-supporting members 13 and 14 (distance between lower surface 16 and lower end 17 shown in FIG. 1)—10 mm;

smallest cross-sectional dimension of each of the two, spaced floss-supporting members 13 and 14 at lower end 17 (shown in FIG. 1)—2 mm;

height of the inner diameter of the split ring portion formed by each of the two finger-engaging members 43 and 44—10 mm;

width of the inner diameter of the split ring portion formed by each of the two finger-engaging members 43 and 44—15 mm;

width of slot 18—2 mm;

smallest cross-sectional dimension of each of the two finger-engaging members 43 and 44 proximate end 15 (shown in FIG. 4A)—2 mm;

distance $d_1$ from upper surface 23 of central base portion 20 to end 15—12 mm; and distance $d_2$ from fixed length of floss 12 to end 15—21 mm.

The resulting floss toy had the above-mentioned dimensions, which made the resulting floss toy suitable for use by an adult.

Example 2

Preparation of a Flossing Device

An exemplary flossing toy 100 as shown in FIGS. 1, 2B, 3B and 4B was prepared using the method as described in Example 1.

overall width (distance between outer edges 25 and 26 shown in FIG. 4B)—14 mm;

overall length (distance between outer edges 21 and 22 shown in FIG. 4B)—8 mm;

overall height (distance between upper end 15 and lower end 17 shown in FIG. 1)—18 mm;

length of fixed length of floss 12—14 mm;

length of each of the two, spaced floss-supporting members 13 and 14 (distance between lower surface 16 and lower end 17 shown in FIG. 1)—8 mm;

smallest cross-sectional dimension of each of the two, spaced floss-supporting members 13 and 14 at lower end 17 (shown in FIG. 1)—2 mm;

height of the inner diameter of the split ring portion formed by each of the two finger-engaging members 43 and 44—7 mm;

width of the inner diameter of the split ring portion formed by each of the two finger-engaging members 43 and 44—10 mm;

width of slot 18—1 mm;

smallest cross-sectional dimension of each of the two finger-engaging members 43 and 44 proximate end 15 (shown in FIG. 4B)—2 mm;

distance $d_1$ from upper surface 23 of central base portion 20 to end 15—9 mm; and distance $d_2$ from fixed length of floss 12 to end 15—17 mm.

The resulting floss toy had the above-mentioned dimensions, which made the resulting floss toy suitable for use by a child.

Example 3

Preparation of a Flossing Device

An exemplary flossing toy 200 as shown in FIGS. 5A-5B was prepared as described in Example 1.

The resulting floss toy had the following dimensions:

overall width (distance between outer edges 25 and 26 shown in FIG. 5A)—13 mm;

overall length (distance between outer edges 21 and 22 shown in FIG. 5A)—20 mm;

overall height (distance between upper end 15 and lower end 17)—18 mm;

length of fixed length of floss 12—13 mm;

length of each of the two, spaced floss-supporting members 13 and 14 (distance between lower surface 16 and lower end 17)—8 mm;

smallest cross-sectional dimension of each of the two, spaced floss-supporting members 13 and 14 at lower end 17—1.5 mm;

height of the inner diameter of the split ring portion formed by each of the two finger-engaging members 43 and 44—7 mm;

width of the inner diameter of the split ring portion formed by each of the two finger-engaging members 43 and 44—10 mm;

width of slot 18—1 mm;

smallest cross-sectional dimension of each of the two finger-engaging members 43 and 44 proximate end 15 (shown in FIG. 5B)—1.0 mm;

distance $d_1$ from upper surface 23 of central base portion 20 to end 15—8.5 mm; and distance $d_2$ from fixed length of floss 12 to end 15—17 mm.

The resulting floss toy had the above-mentioned dimensions, which made the resulting floss toy suitable for use by a child.

Example 4

Preparation of a Flossing Device

An exemplary flossing toy 300 as shown in FIGS. 6A-6B was prepared as described in Example 1.

The resulting floss toy had the following dimensions:

overall width (distance between outer edges 25 and 26 shown in FIG. 6A)—18 mm;

overall length (distance between outer edges 21 and 22 shown in FIG. 6A)—42 mm;

overall height (distance between upper end 15 and lower end 17)—22 mm;

length of fixed length of floss 12—18 mm;

length of each of the two, spaced floss-supporting members 13 and 14 (distance between lower surface 16 and lower end 17)—10 mm;

smallest cross-sectional dimension of each of the two, spaced floss-supporting members 13 and 14 at lower end 17—1.5 mm;

height of the inner diameter of the split ring portion formed by each of the two finger-engaging members 43 and 44—10 mm;

width of the inner diameter of the split ring portion formed by each of the two finger-engaging members 43 and 44—15 mm;

width of slot 18—2 mm;

smallest cross-sectional dimension of each of the two finger-engaging members 43 and 44 proximate end 15 (shown in FIG. 6B)—1.0 mm;

distance $d_1$ from upper surface 23 of central base portion 20 to end 15—12 mm; and distance $d_2$ from fixed length of floss 12 to end 15—21 mm.

The resulting floss toy had the above-mentioned dimensions, which made the resulting floss toy suitable for use by an adult.

Example 5

Preparation of a Flossing Device

Figure 7A:
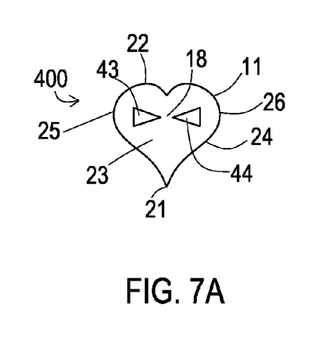
FIGS. 7A-7B depict top and bottom views respectively of another exemplary flossing toy having a heart shape.
Figure 7B:
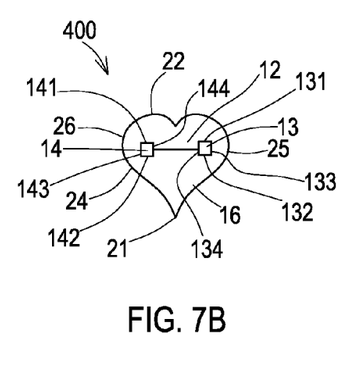

An exemplary flossing toy 400 as shown in FIGS. 7A-7B was prepared as described in Example 1.

The resulting floss toy had the following dimensions:

overall width (distance between outer edges 25 and 26 shown in FIG. 7A)—26 mm;

overall length (distance between outer edges 21 and 22 shown in FIG. 7A)—28 mm;

overall height (distance between upper end 15 and lower end 17)—22 mm;

length of fixed length of floss 12—18 mm;

length of each of the two, spaced floss-supporting members 13 and 14—10 mm;

smallest cross-sectional dimension of each of the two, spaced floss-supporting members 13 and 14 at lower end 17—1.5 mm;

height of the inner diameter of the split ring portion formed by each of the two finger-engaging members 43 and 44—10 mm;

width of the inner diameter of the split ring portion formed by each of the two finger-engaging members 43 and 44—15 mm;

width of slot 18—2 mm;

smallest cross-sectional dimension of each of the two finger-engaging members 43 and 44 proximate end 15—1.0 mm;

distance $d_1$ from upper surface 23 of central base portion 20 to end 15—12 mm; and distance $d_2$ from fixed length of floss 12 to end 15—21 mm.

The resulting floss toy had the above-mentioned dimensions, which made the resulting floss toy suitable for use by an adult.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A flossing toy comprising:
a central base portion defining a horizontal plane,
two, spaced floss-supporting members extending downward from said central base portion,
a fixed length of floss extending between and connected to each of said two, spaced floss-supporting members, wherein said fixed length of floss is substantially equal to or less than an overall width of said flossing toy, and two finger-engaging members extending upward from said central base portion, wherein each of said two finger-engaging members independently comprises (i) a first end connected to said central base portion and (ii) a second end opposite said first end, said two finger-engaging members combining with one another to form an open expandable loop having a disconnecting slot therein, said disconnecting slot being positioned between opposing and separated end surfaces of said second ends of said two finger-engaging members, said disconnecting slot being positioned a distance from said central base portion and a further distance from said fixed length of floss, said open loop being sized to adjustably extend over and grasp a finger positioned therein wherein (i) said central base portion, said two, spaced floss-supporting members, and said two finger-engaging members form a monolithic flossing member, and (ii) said two finger-engaging members and said fixed length of floss extend within a vertical plane transverse to the horizontal plane.

2. The flossing toy of claim 1, wherein (i) opposite ends of said fixed length of floss are embedded within end portions of said two, spaced floss-supporting members, (ii) said fixed length of floss is up to about 1.05 times an overall width of the flossing toy, and (iii) said fixed length of floss remains constant throughout a life of the flossing toy.

3. The flossing toy of claim 2, wherein said disconnecting slot is positioned a maximum distance from said fixed length of floss, said disconnecting slot and said fixed length of floss being on opposite ends of said flossing toy.

4. The flossing toy of claim 1, wherein an amount of tension within said fixed length of floss stays substantially constant during a step wherein an inner perimeter of said open expandable loop is expanded.

5. The flossing toy of claim 3, wherein said central base portion has an outer perimeter that extends horizontally beyond outer front and rear edges of each of said two, spaced floss-supporting members, said front and rear edges being parallel with said fixed length of floss.

6. The flossing toy of claim 5, wherein said outer perimeter extends horizontally beyond all outer edges of each of said two, spaced floss-supporting members.

7. The flossing toy of claim 5, wherein an upper surface of said central base portion, a lower surface of said central base portion, or both said upper and lower surfaces of said central base portion has (i) surface undulations, (ii) printed material, or (iii) both (i) and (ii) thereon.

8. The flossing toy of claim 1, wherein said flossing toy consists of said central base portion, said two, spaced floss-supporting members, said fixed length of floss, said two finger-engaging members, and optional printed material along a surface of said flossing toy.

9. The flossing toy of claim 1, wherein said flossing toy further comprises one or more additive materials coated onto said flossing toy or incorporated into said flossing toy, said one or more additive materials being selected from (i) a fluoride-containing component, (ii) an anti-bacterial component, (iii) a colorant, (iv) a flavor, (v) a scent, or (vi) any combination or (i) to (v).

10. A flossing toy comprising:
a central base portion defining a horizontal plane,
two, spaced floss-supporting members extending downward from said centralbase portion, a fixed length of floss extending between and connected to each of said two, spaced floss-supporting members, and two finger-engaging members extending upward from said central base portion, wherein each of said two finger-engaging members independently comprises (i) a first end connected to said central base portion and (ii) a second end opposite said first end, said two finger-engaging members combining with one another to form an open expandable loop having a disconnecting slot therein, said disconnecting slot being positioned between opposing and separated end surfaces of said second ends of said two finger-engaging members, said disconnecting slot being positioned a distance from said central base portion and a further distance from said fixed length of floss, said open loop being sized to adjustably extend over and grasp a finger positioned therein, wherein (I) said central base portion, said two, spaced floss-supporting members, and said two finger-engaging members form a monolithic flossing member, (II) said central base portion has an outer perimeter that extends horizontally beyond outer front and rear edges of each of said two, spaced floss-supporting members, said front and rear edges being parallel with said fixed length of floss and (III) said two finger-engaging members and said fixed length of floss extend within a vertical plane transverse to the horizontal plane.

11. The flossing toy of claim 10, wherein (I) said disconnecting slot is positioned a maximum distance from said fixed length of floss, said disconnecting slot and said fixed length of floss being on opposite ends of said flossing toy, and (II) an amount of tension within said fixed length of floss stays substantially constant during a step wherein an inner perimeter of said open expandable loop is expanded.

12. The flossing toy of claim 11, wherein (i) opposite ends of said fixed length of floss are embedded within end portions of said two, spaced floss-supporting members, (ii) said fixed length of floss is up to about 1.05 times an overall width of the flossing toy, and (iii) said fixed length of floss remains constant throughout a life of the flossing toy.

13. The flossing toy of claim 11, wherein said flossing toy further comprises one or more additive materials coated onto said flossing toy or incorporated into said flossing toy, said one or more additive materials being selected from (i) a fluoride-containing component, (ii) an anti-bacterial component, (iii) a colorant, (iv) a flavor, (v) a scent, or (vi) any combination or (i) to (v).

14. The flossing toy of claim 10, wherein said two finger-engaging members and said fixed length of floss are within a plane.

15. A flossing toy consisting of:
a central base portion defining a horizontal plane,
two, spaced floss-supporting members integrally connected to and extending downward from said central base portion,
a fixed length of floss extending between and connected to each of said two, spaced floss-supporting members, wherein (i) opposite ends of said fixed length of floss are embedded within end portions of said two, spaced floss-supporting members, (ii) said fixed length of floss is up to about 1.05 times an overall width of the flossing toy, and (iii) said fixed length of floss remains constant throughout a life of the flossing toy,
two finger-engaging members integrally connected to and extending upward from said central base portion, wherein each of said two finger-engaging members independently comprises (i) a first end connected to said central base portion and (ii) a second end opposite said first end, said two finger-engaging members combining with one another to form an open expandable loop having a disconnecting slot therein, said disconnecting slot being positioned between opposing and separated end surfaces of said second ends of said two finger-engaging members, said disconnecting slot being positioned a distance from said central base portion and a further distance from said fixed length of floss, and said open loop being sized to adjustably extend over and grasp a finger positioned therein, said two finger-engaging members and said fixed length of floss extend within a vertical plane transverse to the horizontal plane, and one or more additive materials coated onto said flossing toy or incorporated into said flossing toy, said one or more additive materials being selected from: (i) a fluoride-containing component, (ii) an anti-bacterial component, (iii) a colorant, (iv) a flavor, (v) a scent, or (vi) any combination thereof.

16. The flossing toy of claim 15, wherein at least one of said one or more additive materials is present on said flossing toy.

17. The flossing toy of claim 16, wherein said one or more additive materials comprises a flavor.

18. The flossing toy of claim 15, wherein said two finger-engaging members and said fixed length of floss are within a plane.

19. The flossing toy of claim 15, wherein said one or more additive materials comprises a flavor.

\* \* \* \* \*